US012642933B2

(12) United States Patent
Freeman et al.

(10) Patent No.: US 12,642,933 B2
(45) Date of Patent: Jun. 2, 2026

(54) GAS DELIVERY SYSTEM

(71) Applicant: Vanessa Lin

(72) Inventors: Michelle Lynn Freeman, Jacksonville, FL (US); Kevin Thomas Riutort, Ponte Vedra Beach, FL (US); Klaus Dieter Torp, Atlantic Beach, FL (US); John C. Lin, Seaford, VA (US); Benjamin John Nickless, Newport News, VA (US); Michael Andrew Park, Norfolk, VA (US); Kingsley Chauncey Wu, Yorktown, VA (US)

( * ) Notice: Subject to any disclaimer, the term of this patent is extended or adjusted under 35 U.S.C. 154(b) by 967 days.

(21) Appl. No.: 17/863,252

(22) Filed: Jul. 12, 2022

(65) Prior Publication Data

US 2023/0010008 A1     Jan. 12, 2023

Related U.S. Application Data

(60) Provisional application No. 63/220,759, filed on Jul. 12, 2021.

(51) Int. Cl.
*A61M 16/06*      (2006.01)
*A61M 16/08*      (2006.01)
*A61M 16/10*      (2006.01)

(52) U.S. Cl.
CPC .... *A61M 16/0672* (2014.02); *A61M 16/0683* (2013.01); *A61M 16/0816* (2013.01);
(Continued)

(58) Field of Classification Search
CPC .......... A61M 16/0666; A61M 16/0672; A61M 16/0677; A62B 18/003
See application file for complete search history.

(56) References Cited

U.S. PATENT DOCUMENTS

| | | | | |
|---|---|---|---|---|
| 4,278,082 A | * | 7/1981 | Blackmer | ......... A61M 16/0672 |
| | | | | 128/207.18 |
| 4,406,283 A | * | 9/1983 | Bir | .................... A61M 16/0672 |
| | | | | 128/207.18 |

(Continued)

FOREIGN PATENT DOCUMENTS

| | | |
|---|---|---|
| DE | 19841070 | 5/2000 |
| EP | 0053449 | 6/1982 |

(Continued)

OTHER PUBLICATIONS

Miller et al. ("Computational Fluid Dynamics Modeling . . . High Flow Nasal Cannula Design Elements", https://www.academia.edu/download/115385869/computational-fluid-dynamics-modeling-of-extrathoracic-airway-flush-evaluation-of-high-flow-nasal-cannula-design-elements-2161-105X-1000.pdf) Access, Jul. 2025 (Year: 2016).*

(Continued)

*Primary Examiner* — Joseph D. Boecker
*Assistant Examiner* — Jaeick Jang
(74) *Attorney, Agent, or Firm* — Schwegman Lundberg & Woessner, P.A.

(57) ABSTRACT

A gas delivery system, for providing gas to a wearer, includes a first body having a first cavity. The first body is supportable to a side of a nose and mouth of the wearer. A first adapter receives gas from a gas supply and provide the gas to the first cavity. A plurality of first openings in the first body to create a bolus of gas about the nostrils of the nose and the mouth. The first body, and a second similar body may be supported by an adjustable bridge on opposite sides of the nose and mouth of the wearer.

21 Claims, 10 Drawing Sheets

(52) U.S. Cl.
CPC ...... *A61M 16/085* (2014.02); *A61M 16/1005* (2014.02); *A61M 2016/0661* (2013.01); *A61M 2230/42* (2013.01)

(56) References Cited

U.S. PATENT DOCUMENTS

| | | | |
|---|---|---|---|
| 6,328,038 B1 | 12/2001 | Kessler et al. | |
| 6,439,235 B1 | 8/2002 | Larquet et al. | |
| 2002/0092527 A1* | 7/2002 | Wood | A61M 16/0666 128/206.13 |
| 2005/0217668 A1 | 10/2005 | Figley et al. | |
| 2006/0278232 A1 | 12/2006 | Nichols | |
| 2010/0252037 A1 | 10/2010 | Wondka et al. | |
| 2011/0214676 A1* | 9/2011 | Allum | A61M 16/085 128/207.18 |
| 2012/0271187 A1 | 10/2012 | Mcneill | |
| 2014/0102442 A1* | 4/2014 | Wilson | F24F 9/00 128/200.28 |
| 2014/0209099 A1 | 7/2014 | Barker | |
| 2016/0095996 A1* | 4/2016 | Gusky | A61M 16/0816 128/205.25 |
| 2016/0263340 A1* | 9/2016 | Fenwick | A61M 16/06 |
| 2017/0028230 A1* | 2/2017 | Brose | A62B 17/04 |
| 2017/0361054 A1* | 12/2017 | Day | A42B 1/048 |

FOREIGN PATENT DOCUMENTS

| | | | | |
|---|---|---|---|---|
| KR | 101940638 B1 * | 1/2019 | | A62B 18/003 |
| KR | 20200120401 A * | 10/2020 | | F24F 8/194 |

OTHER PUBLICATIONS

Machine translation of KR-20200120401-A. Access from PE2E on Dec. 2025 (Year: 2019).*

"International Application Serial No. PCT US2022 036854, International Search Report mailed Oct. 31, 2022", 9 pgs.

"International Application Serial No. PCT US2022 036854, Written Opinion mailed Oct. 31, 2022", 7 pgs.

International Application Serial No. PCT/US2022/036854, International Preliminary Report on Patentability mailed Jan. 25, 2024, 9 pgs.

* cited by examiner

GAS DELIVERY SYSTEM

RELATED APPLICATION

This application claims priority to U.S. Provisional Application Ser. No. 63/220,759 (entitled Oxygen Delivery System, filed Jul. 12, 2021 which is incorporated herein by reference.

STATEMENT OF GOVERNMENT RIGHTS

The invention described herein was made in part by an employee of the United States Government and may be manufactured and used by or for the United States Government for Governmental purposes without payment of royalties thereon or therefore.

BACKGROUND

Prior devices that provide oxygen to people with inadequate oxygen levels utilize devices that block the patient's nose and mouth, preventing normal speech, eating, and drinking functions. Examples of prior devices include the use oxygen line connected cannula supported inside the nostrils of a patient or various types of masks or face tents that cover the nose and mouth of the patient. One prior device includes an arm that extends from a head mounted support in front of the mouth and nose of the patient. Such prior devices may be somewhat invasive leading to patient discomfort and may also exacerbate sensations of claustrophobia. The devices may also cause distress in those patients emerging from anesthesia and can also be loud.

SUMMARY

A gas delivery system, for providing gas to a wearer, includes a first body having a first cavity. The first body is supportable to a side of a nose and mouth of the wearer. A first adapter receives gas from a gas supply and provide the gas to the first cavity. A plurality of first openings in the first body to create a bolus of gas about the nostrils of the nose and the mouth. The first body, and a second similar body may be supported by an adjustable bridge on opposite sides of the nose and mouth of the wearer.

DETAILED DESCRIPTION

In the following description, reference is made to the accompanying drawings that form a part hereof, and in which is shown by way of illustration specific embodiments which may be practiced. These embodiments are described in sufficient detail to enable those skilled in the art to practice the invention, and it is to be understood that other embodiments may be utilized and that structural, logical and electrical changes may be made without departing from the scope of the present invention. References to directions should be interpreted in the context of a person normally wearing the described system and devices, with vertical corresponding to the direction generally from the mouth to the nostrils of a wearer. The following description of example embodiments is, therefore, not to be taken in a limited sense, and the scope of the present invention is defined by the appended claims.

Current devices that provide oxygen to a wearer, such as a patient with inadequate oxygen levels utilize devices that block the wearer's nose and mouth, preventing normal speech, eating, and drinking functions. Current systems may also be somewhat invasive leading to wearer discomfort. may exacerbate sensations of claustrophobia, can cause distress in those wearers emerging from anesthesia, and can be loud.

An improved oxygen delivery system is designed to allow normal speech, eating, and drinking, with minimal discomfort, while providing efficient, concentrated oxygen delivery to the wearer's nose and mouth. The oxygen delivery system may be useful for oxygen delivery during medical procedures requiring access to a wearer's mouth and airway, which increases wearer safety during such medical procedures that require intra-venous sedation.

Figure 1:
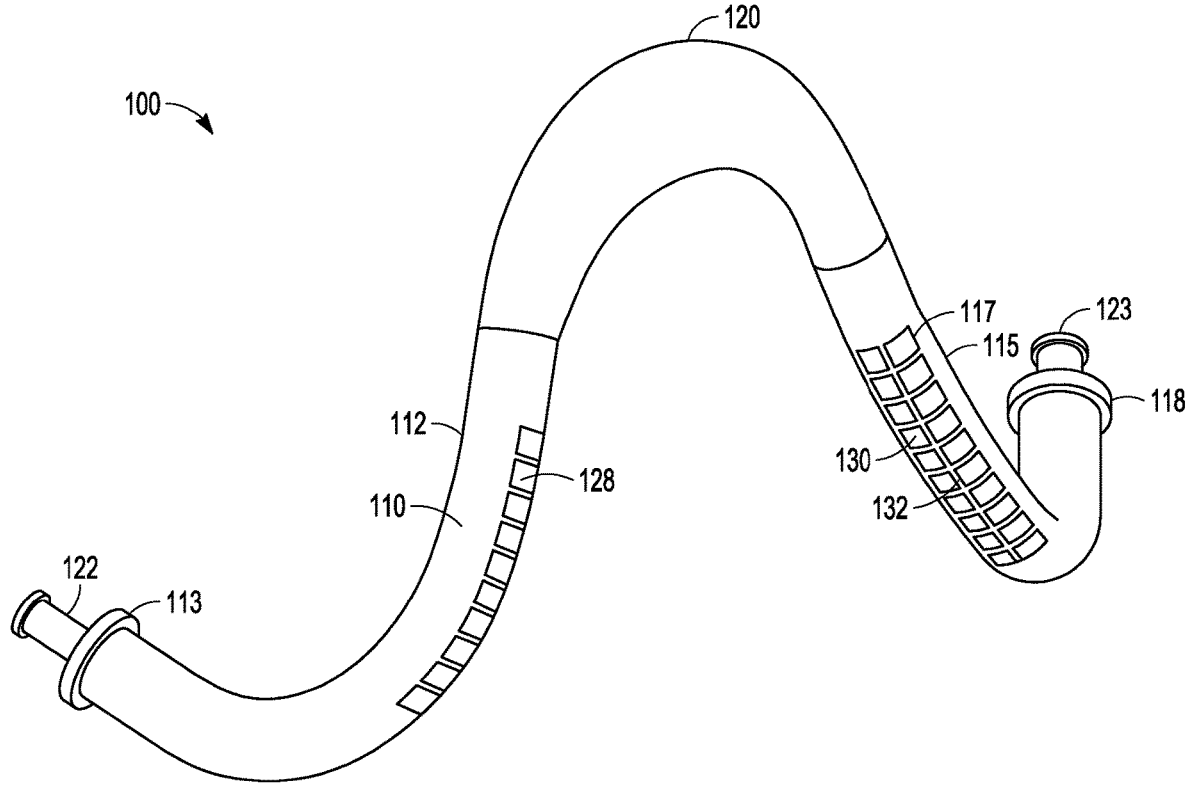
FIG. 1 is a perspective representation of an improved oxygen delivery system according to an example embodiment.

FIG. 1 is a perspective representation of an improved oxygen delivery system 100 provides for directed oxygen flow concentrated at a wearer's nose and mouth. While providing oxygen, the oxygen delivery system 100 also allows the wearer to eat and drink normally. The oxygen delivery system 100 is composed of two perforated hollow conduits 110 and 115 that are supported somewhat vertically on both sides of the wearer's face alongside their mouth and nose. The conduits 110 and 115 have top ends 112 and 117 supported by a flexible bridge 120 that may be molded to fit the wearer's nose. The bridge 120 may also be hollow to provide a conduit that extends through the bridge into both conduits 110 and 115.

The conduits 110 and 115 may curve outward from the wearer's nose towards and outside edges of the wearer's mouth in one example. Bottom ends 113 and 118 of the conduits 110 and 115 may flair and angle back toward ears of the wearer. The bottom ends 113 and 118 are also hollow and may be coupled to an oxygen source, such as a hospital's oxygen supply system or a mobile oxygen supply via standard interfaces 122 and 123 to supply lines. The conduits 110 and 115 include perforations 128 and 130 that are shaped and oriented to direct oxygen flow from the hollow tubes towards and over the wearer's nose and mouth.

In one example, the oxygen supply lines may be coupled to the interfaces 122 and 123 and extend like eyeglass stems over the ears of the wearer to provide additional support to keep the bridge 120 on the wearer's nose such that the perforations 128 and 130 are positioned between the nose nostril openings and the mouth of the wearer. Perforations positioned near the nostrils are closer to the nose, which the curvature of the conduits 110 and 115 results in perforations by the mouth to be further away from a vertical line drawn down from the nose. In one example, the perforations are simply arcuate rectangular portions cut from the tube that are angled to direct the air between the nostrils and mouth to create a cloud of oxygen rich gas to be breathed in by the wearer.

A portion of the conduit tube running axially along the perforations and referred to as an axial support 132, may provide support, with perforations on either side of the support 132. The angle of the perforations on the tubes may be between 20 and 90 degrees outward from the face of a wearer wearing the oxygen delivery system 100 in one example. The oxygen delivery system 100 thus provides a good balance between wearer comfort and the necessary oxygen levels near the nostril and mouth.

The oxygen delivery system 100 with perforations 128, 130 may provide a more homogeneous localized jet-flow mixing that enables significant reduction in noise associated with typical jet nozzles.

Figure 2:
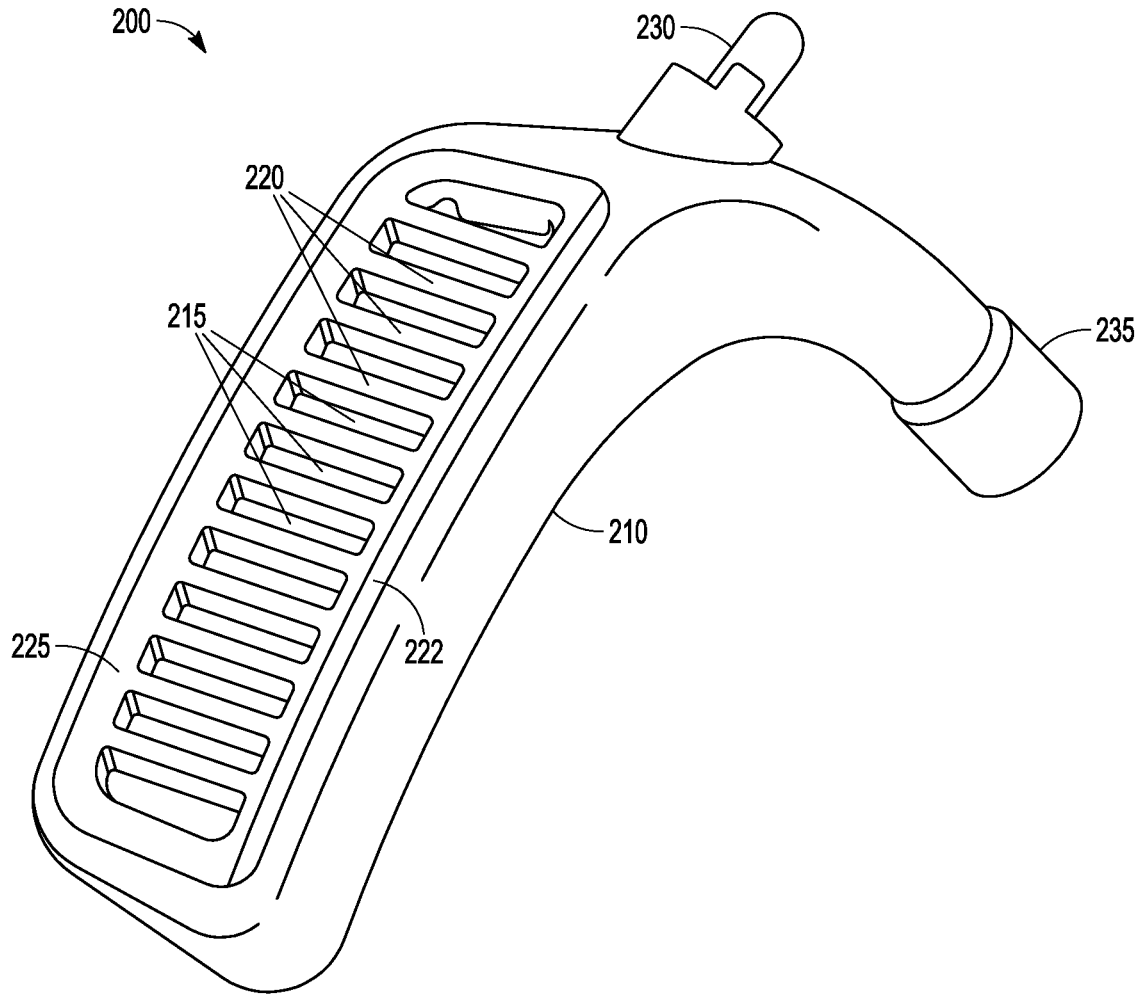
FIG. 2 is a perspective view of an alternative oxygen delivery system according to an example embodiment.
Figure 3:
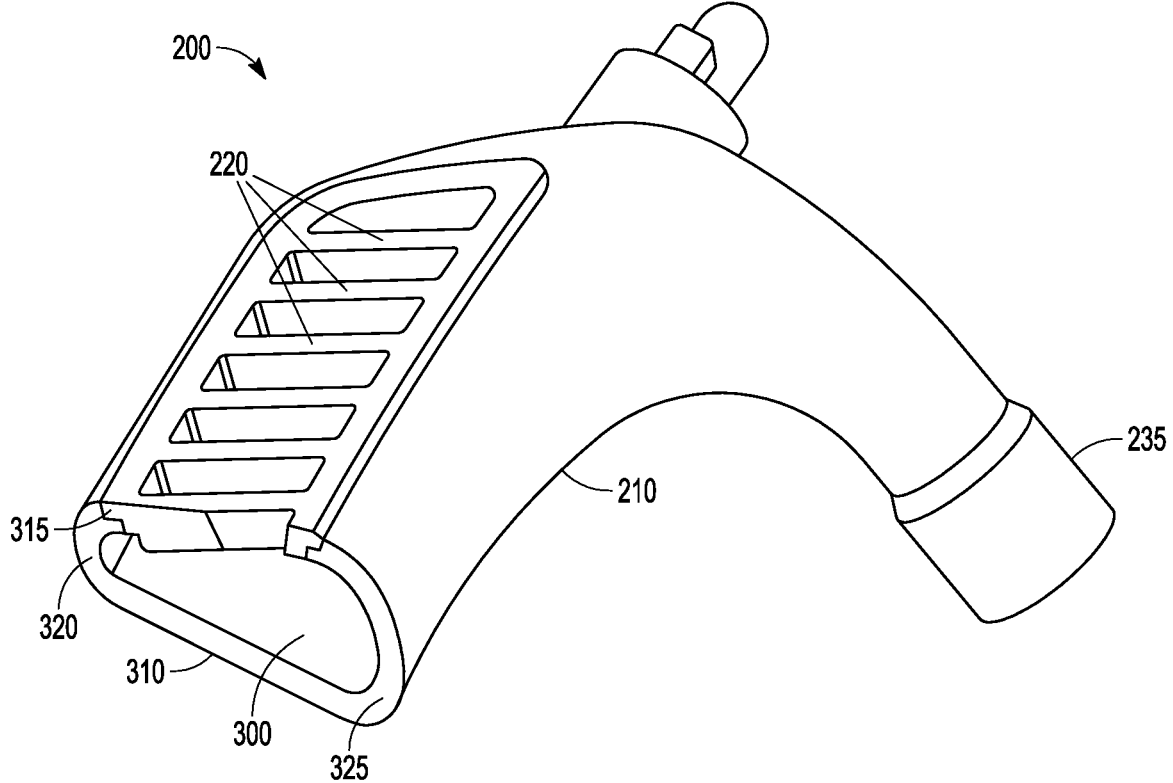
FIG. 3 is a perspective view of the alternative oxygen delivery system with a portion cut away to illustrate an interior of the oxygen delivery system according to an example embodiment.
Figure 4:
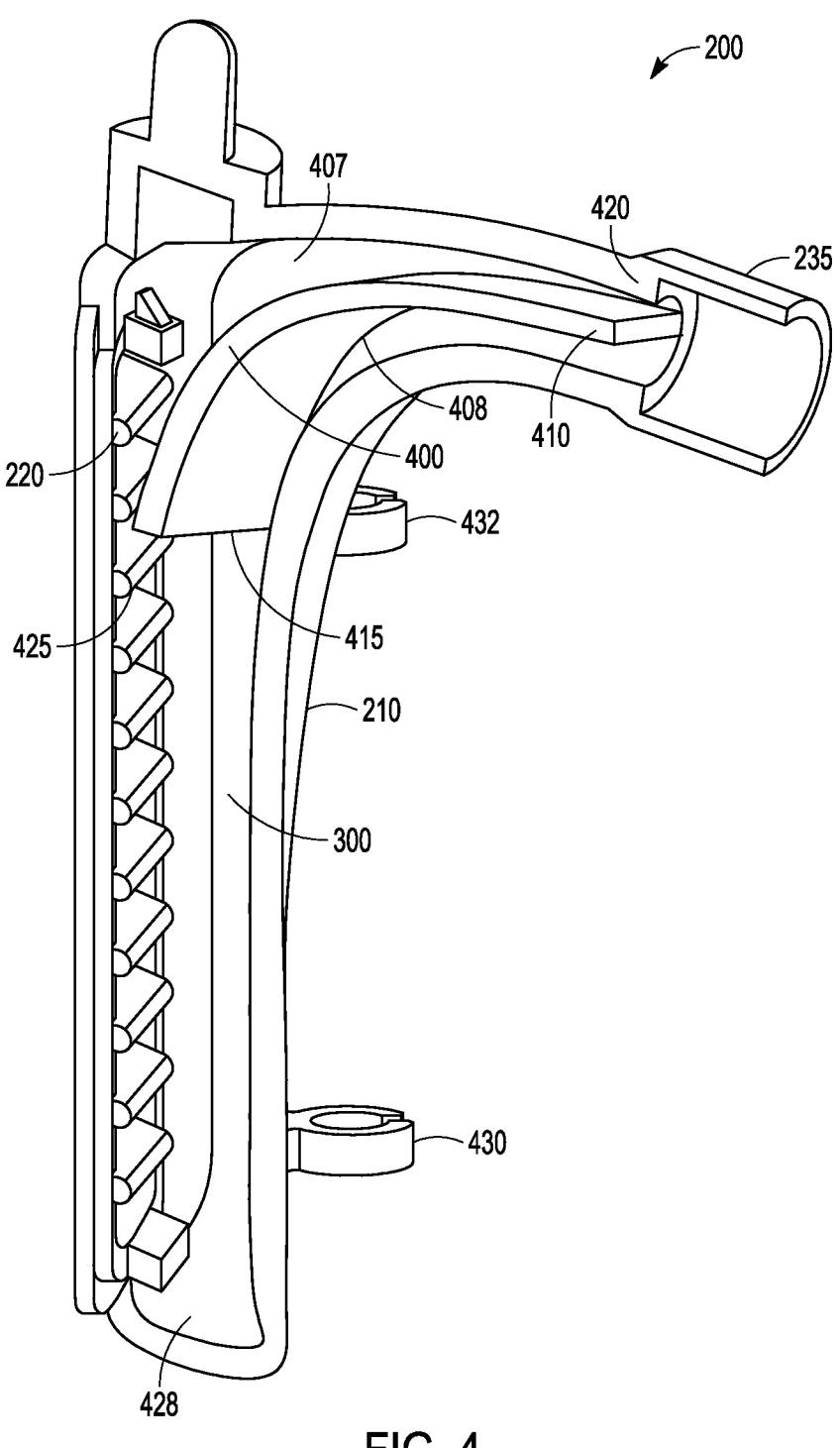
FIG. 4 is a perspective view of the alternative oxygen delivery system with an axial cut along an entire length of the oxygen delivery system according to an example embodiment.

FIG. 2 is a perspective view of an alternative oxygen delivery system 200. FIG. 3 is a perspective view of the oxygen delivery system 200 with a portion cut away to illustrate an interior of the oxygen delivery system 200. FIG. 4 is a perspective view of the oxygen delivery system 200 with an axial cut along an entire length of the oxygen delivery system 200. The Oxygen delivery system 200 includes a conduit, referred to as body 210 and multiple exits or openings 215 in the body 210 separated by louvers 220 for conducting gas, such as oxygen to an area in front of a wearer's mouth and nose. The body 210 may include an opening 222 sized to fit a louvered grating 225 that includes the openings 215 and louvers 220. The louvered grating 225 may be secured in the opening 222. Body 210 includes a nub 230 positioned at a top of the body 210 for coupling to a nosepiece, such as nosepiece 120. A second body, not shown, may be a mirror image of body 210 for coupling to an opposite end of the nosepiece 120. The nub 230 may be positioned such that when coupled to the nosepiece 120, the louvers 220 are positioned to direct air between the nostrils and the mouth. Body 210 curves and tapers to a coupler 235 for coupling to a gas supply, such as an oxygen tube.

FIG. 3 illustrates a cavity 300 that acts as a plenum for transporting and distributing oxygen (O2) or other desired gas to an area in front of a wearer's mouth and nose. The cavity 300 is an open space designed to hold gas, such as oxygen at a higher than atmospheric pressure to deliver the oxygen to the wearer. The cavity 300 is somewhat triangular shaped, having three sides that intersect with rounded corners in one example to optimize airflow through the plenum. A first side 310 is fairly straight and meets a second side 315 at a point 320 farthest from the mouth and nose of the wearer. The second side 315 includes the opening 222 and louvered grating 225 and extends back toward a third side 325 that is positioned closest to the wearer when worn. An angle between the first side 310 and second side 315 may be between 10 and 30 degrees in one example. The opening proximate point 320, the intersection of the first and second sides is the narrowest portion of the opening. A channel 330 may be formed along a side of the louvered grating 225 allow for more gas flow. Side 325 may be arcuate in shape forming a concave rounded portion of the cavity 300. One can also see in FIG. 3 that the louvers 220 are angled slightly upward toward the mouth and nose when worn to provide a better bolus of gas in front of the mouth and nose.

FIG. 4 illustrates the upward angle of the louvers 220, which may be angled about 2-10 degrees upward toward the mouth and nostrils from horizontal in one example. The louvers 220 may all be angled the same amount, or the angles may vary to redirect airflow to create an improved bolus of gas about the mouth and nostrils.

A deflector plate, referred to as a baffle 400 extends in the direction of gas flow through a portion of the cavity 300 of the body 210 to divert the gas flow in a desired manner toward the exits and louvers 220. The baffle 400 is a smooth, concave, curving plate in one example that helps to deflect or divert more gas to the lower louvers which supply the mouth area, as opposed to the upper louvers. In one example the louver divides the cavity 300 into an upper cavity portion 407 and a lower cavity portion 408. The upper and lower cavity portions extend from a top end 410 to a bottom end 415 of the baffle 400. The bottom end extends about to a third louver 222 from the top in one example. The length of the baffle 400 may be adjusted in further examples for different louver and corresponding openings between louvers to optimize the creation of gas about the nostrils and mouth of the wearer.

The louver's 220 may extend into the cavity 405 and may have smooth and curved edges 425 to help reduce turbulence. In various examples, the louvers or flaps may be molded with the body 210 or may be hinged or otherwise angularly adjustable to redirect oxygen flow. The baffle 400 is also smooth to help reduce turbulence. By dividing the cavity 405 into upper and lower cavity portions 407 and 408, gas flow becomes more laminar within the cavity, resulting is less turbulence. Since turbulence cause noise, each of these turbulence reducing features helps to minimize noise generated during use of the gas or oxygen delivery system 200.

Coupler 235 may be configured to connect to oxygen supply tubing in one example. Coupler 235 may have an inner diameter that is slightly larger than the cavity diameter as illustrated at a ledge 420 where the coupler 235 meets the body 210. In one example, the body tapers into a round shape with a diameter D1 at ledge 420. Supply tubing may be retentatively inserted into the coupler 235 until it contacts the ledge 420. In one example, making an inner diameter of such tubing equal to diameter D1 ensures the transition between the tubing and the cavity 300 is smooth, minimizing turbulence. Note that end 410 of the baffle 400 may coincide with the ledge 420 and may also have a rounded edge. The cavity 300 may also taper into a smaller cross section toward a bottom 428. The cavity 300 may slightly enlarge at the bottom 428 and also include a rounded and smooth inner surface to further minimize turbulence.

Computational Fluid Dynamics (CFD) may be used to improve the flow inside the device to uniformly deliver oxygen to the exits or vents. Regions of flow separation may be reduced by aligning the baffle 400 to the flow direction calculated with CFD. The outflow exits and louvers may be designed to provide oxygen to the nose and mouth while reducing the entrainment of ambient air.

One or more clips 430, 432 may be positioned along an outside of the body 210, such as a side of the body 210 facing away from a wearer. The clips may be used to hold tubing to collect exhausted air from the wearer and transport such air to one or more gas sensors, such as carbon dioxide sensors.

Figure 5:
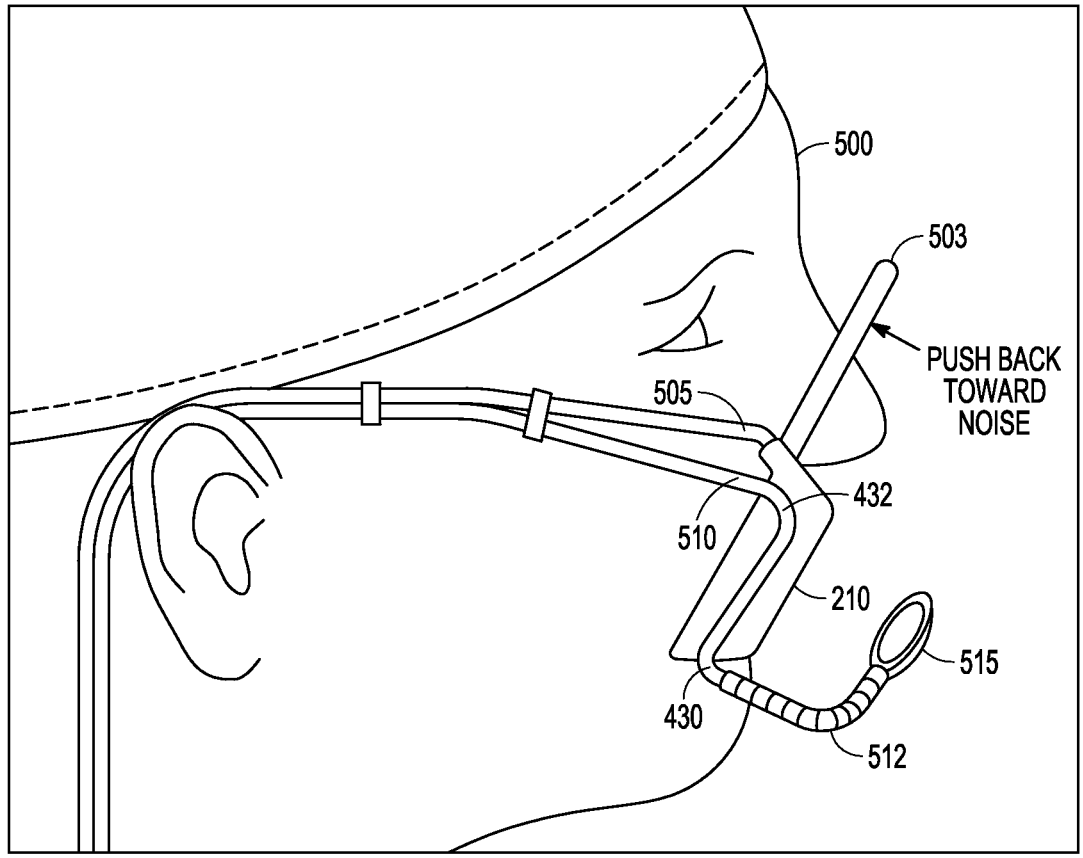
FIG. 5 is a side perspective view of a wearer or patient wearing an oxygen deliver system according to an example embodiment.

FIG. 5 is a side perspective view of a wearer or wearer 500 wearing an oxygen delivery system. A bridge 503 is shown supporting body 210 about the mouth and nostrils of wearer 500. Oxygen may be provided by a tube 505 coupled to provide oxygen to the cavity inside body 210. A second body, not shown, may be similarly coupled to the bridge 503 and oxygen supply tube.

In one example, an optional collection tube 510 is coupled to the body 210 by clips 430 and 432. The collection tube 510 includes an adjustable capturing arm 512 that can be used to position a collector scoop 515 about the nostrils and mouth to collect air exhaled by the wearer 500. In one example, the arm 512 is all plastic segments with ball/socket joints, so that it is adjustable and MRI compatible (no metal). The scoop 515 on the end of the arm captures the exhaled breath. The collection tube 510 may route the collected air to a gas analyzer that may include a carbon dioxide sensor in one example. The clips 430 and 432 allow easy assembly and removal without interrupting oxygen supply, to enable the wearer to eat, drink, and talk, while still receiving oxygen. Measuring $CO_2$ concentrations proximate the wearer's mouth and nostrils provides information useful for determining a respiration rate of the wearer based on measured $CO_2$ fluctuations. For example, exhausted air will have a higher $CO_2$ concentration than gas sampled while the wearer is breathing in. The number of such fluctuations per period of time may be used to determine the respiration rate.

In addition to reducing noise by smoothing passages, the oxygen delivery system also allows access to remove irritants from the nostrils as well as procedural access to the mouth/airway during oxygen delivery. Safety may also be improved by reducing rebreathing of carbon dioxide compared to closed masks.

The length of the body and corresponding louvers may be adjusted from small to medium to large to optimize oxygen (O2). In one example, the length of the wearers nose may be used to select the best size for the wearer. The louvers and corresponding exits may be positioned to lie between an end of the nostrils and an edge of the mouth in one example to create an oxygen cloud to be breathed in by either the mouth or nose. 2-15 liters per minute of oxygen may be flowed for proper respiration.

Figure 6:
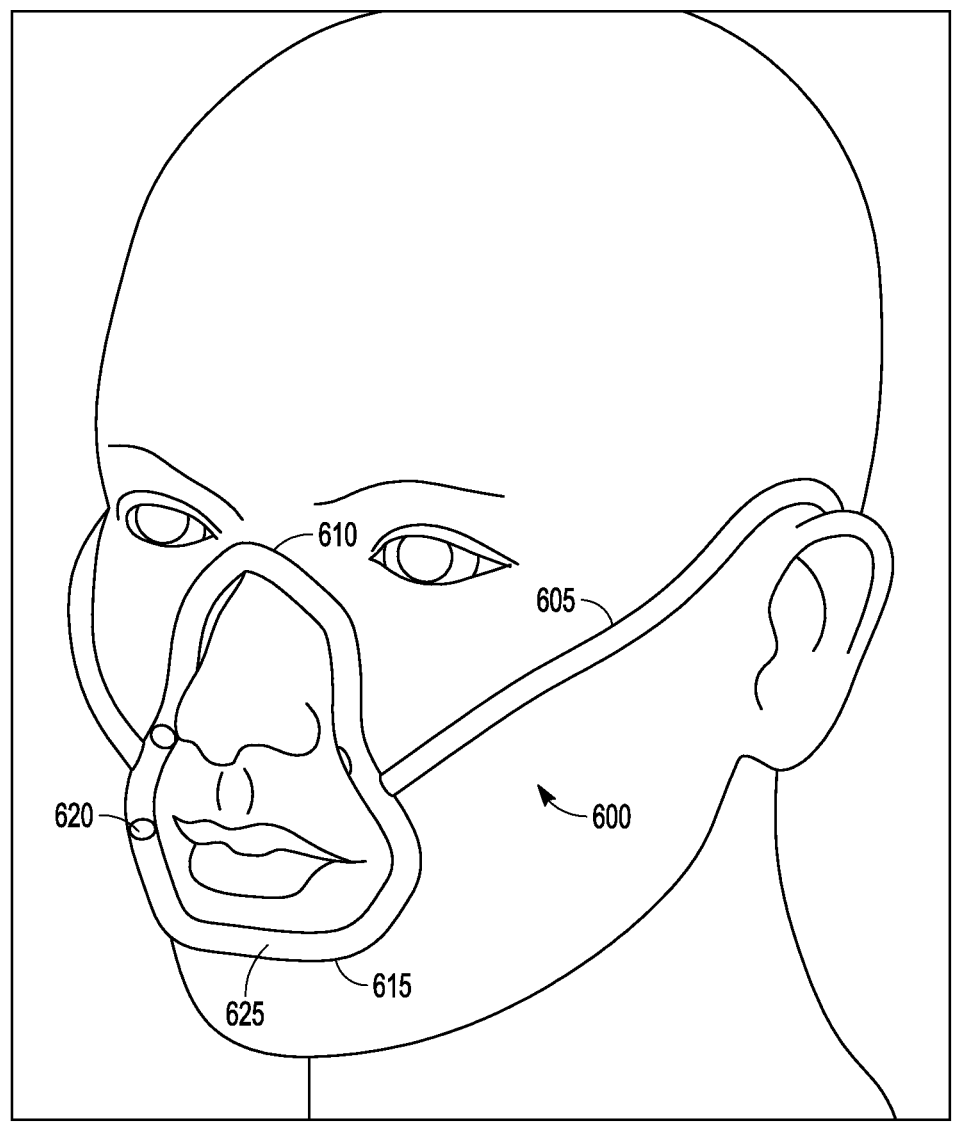
FIG. 6 is a perspective view of an alternative oxygen delivery system according to an example embodiment.

FIG. 6 is a perspective view of an alternative oxygen delivery system 600 according to an example embodiment. System 600 includes stem conduits 605 configured to fit around ears of a wearer and receive gas at a first end near the ear or ears and convey the gas toward the wearer's mouth and nose. System 600 includes a bridge conduit portion 610 and gas delivery conduits 615 that contain perforations 620 and 625 to deliver the gas about the mouth and nose of the wearer. In one example the bridge conduit portion 610 and gas delivery conduits are all interconnected hollow conduits coupled in a loop over the nose of the wearer on a top portion, with side portions configured to be as wide or wider than the mouth of the wearer and a bottom portion extending below the mouth. Perforations 620 are positioned to the side of the mouth and nose, with perforation or perforations 625 positioned in the bottom portion below the mouth.

Figure 7:
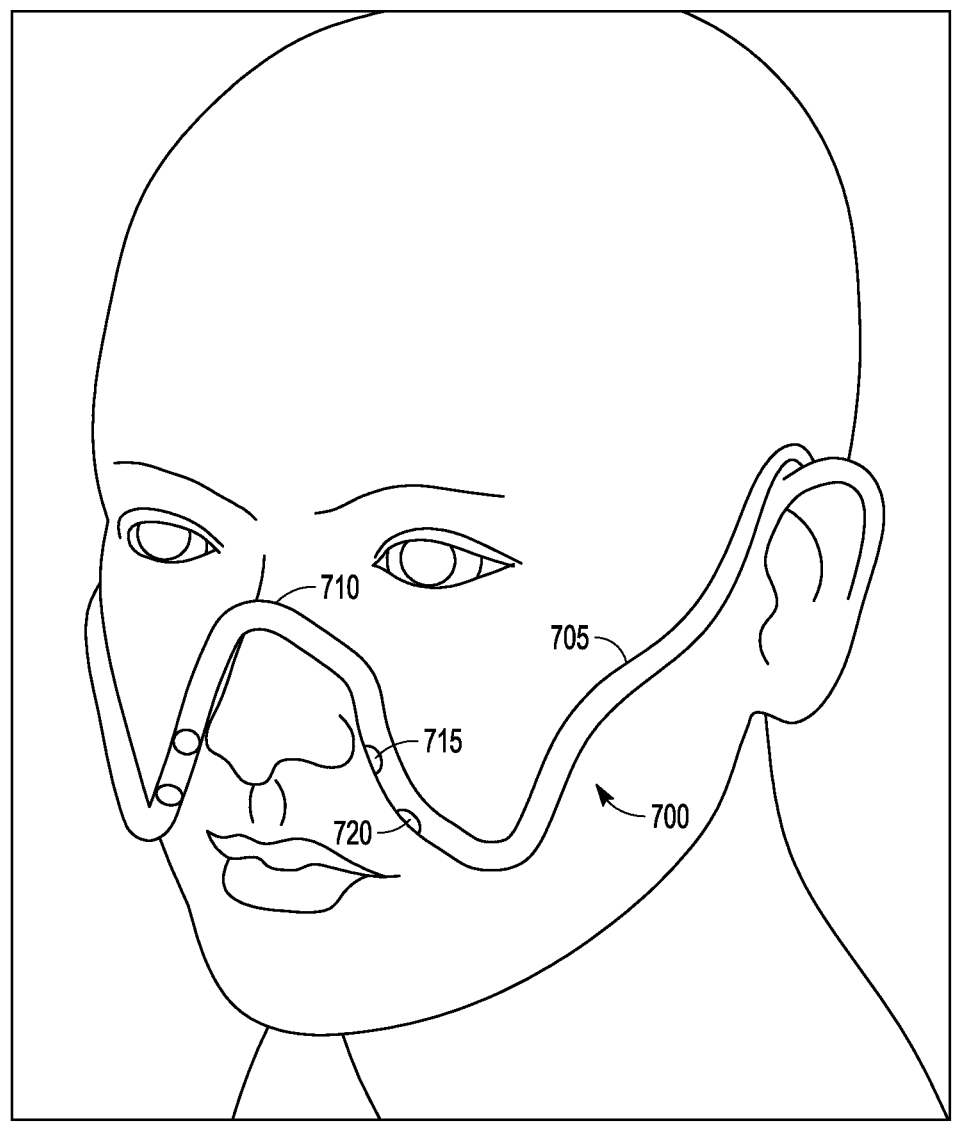
FIG. 7 is a perspective view of an alternative oxygen delivery system according to an example embodiment.
Figure 8:
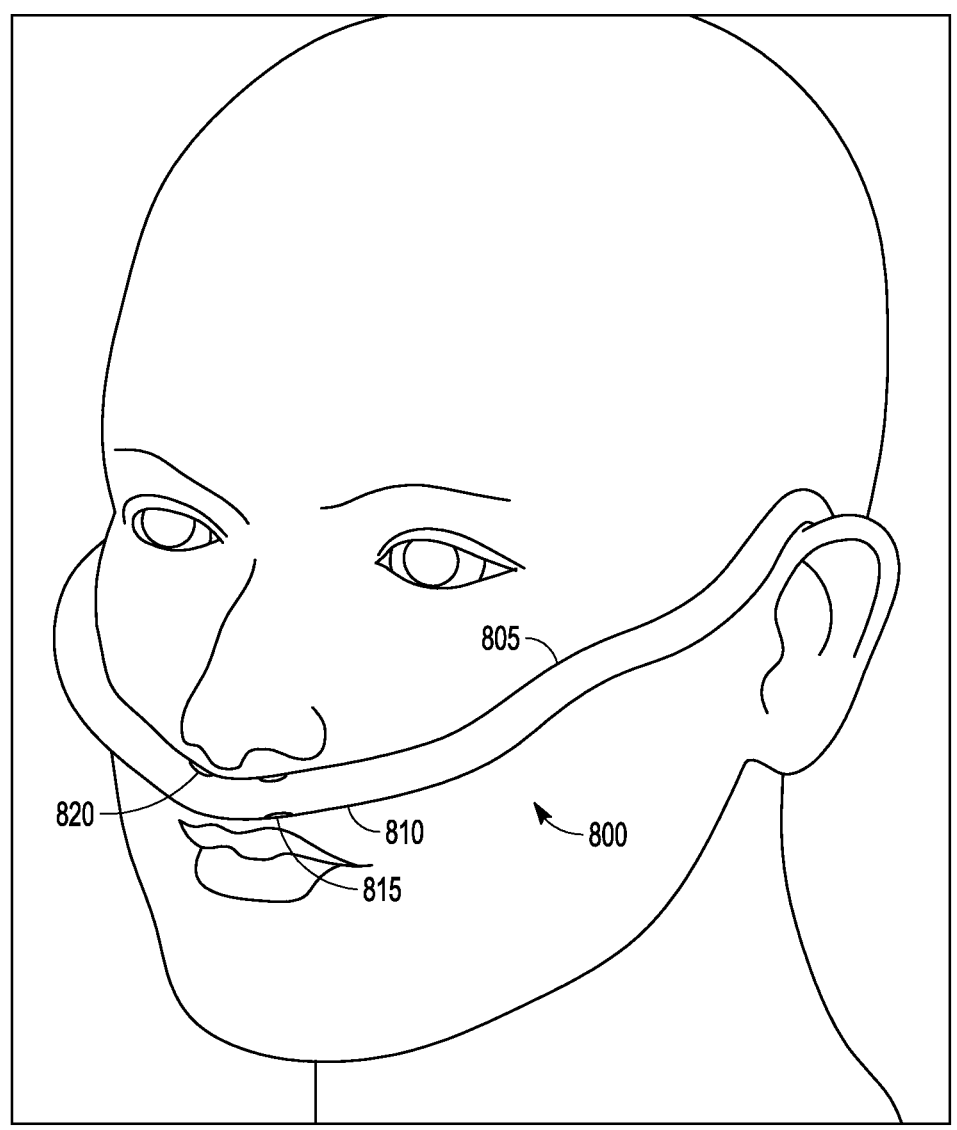
FIG. 8 is a perspective view of an alternative oxygen delivery system according to an example embodiment.

FIG. 7 is a perspective view of an alternative oxygen delivery system 700 according to an example embodiment. System 700 includes stem conduits 705 configured to fit around ears of a wearer and receive gas at a first end near the ear or ears and convey the gas toward the wearer's mouth and nose. System 700 includes a bridge conduit portion 710 and gas delivery conduits 715 that contain perforations 720 to deliver the gas about the mouth and nose of the wearer. In one example the bridge conduit portion 710 and gas delivery conduits 715 are all interconnected hollow conduits coupled in a loop over the nose of the wearer on a top portion, with side portions configured to be as wide or wider than the mouth of the wearer. Perforations 720 are positioned to the side of the mouth and nose FIG. 8 is a perspective view of an alternative oxygen delivery system 900 according to an example embodiment. System 800 includes stem conduits 805 configured to fit around ears of a wearer and receive gas at a first end near the ear or ears and convey the gas toward the wearer's mouth and nose. System 800 includes a gas delivery conduit portion 810 that contains perforations 815 and 820 to deliver the gas between the mouth and nose of the wearer. In one example the gas delivery conduit 810 runs between the mouth and nose of the wearer. Perforations 815 are positioned on a bottom of the conduit 810 to direct gas to the mouth of the wearer. Perforations 820 are positioned on a top of the conduit 810 to direct gas to the nose of the wearer. By being positioned between the mouth and nose of the wearer, the conduit 810 does not interfere with access to the mouth of the wearer, yet creates a bolus of gas about the nostrils of the nose and the mouth of the wearer.

Figure 9:
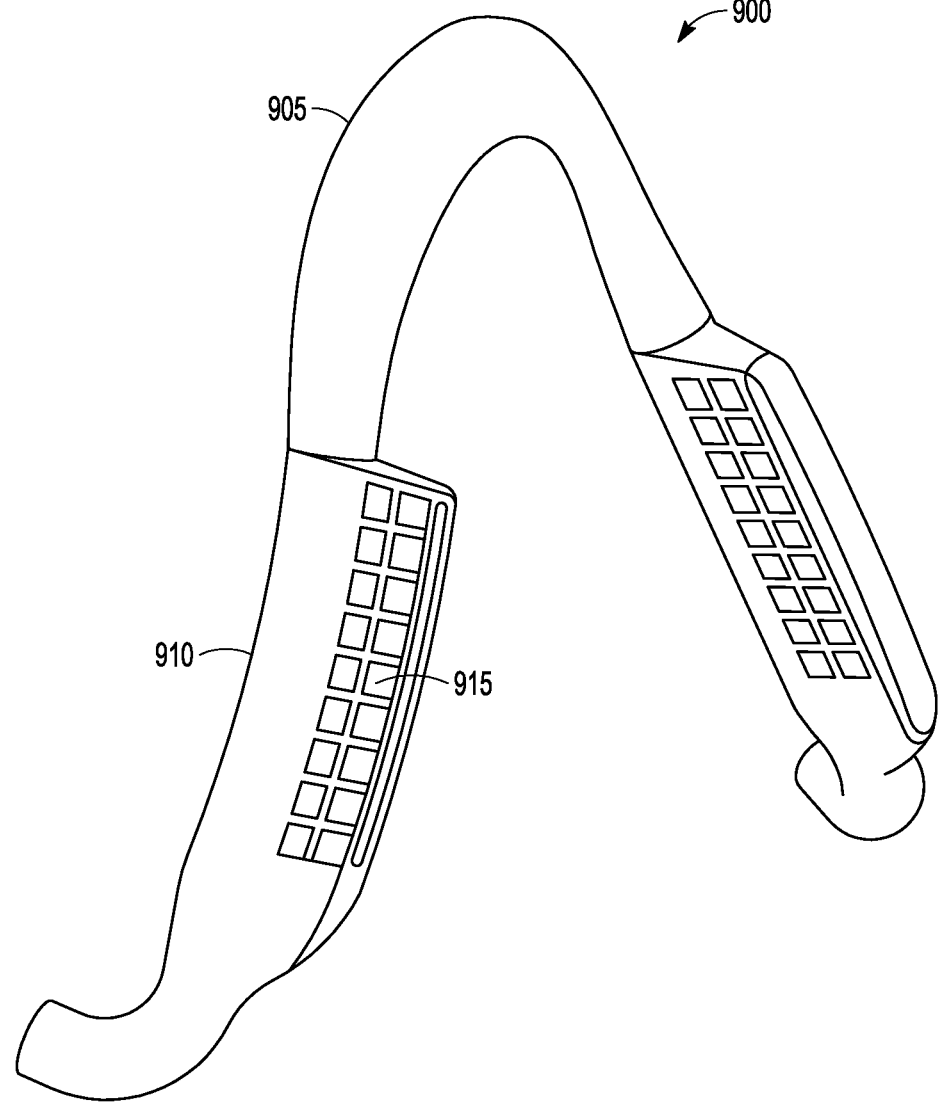
FIG. 9 is a perspective view of an alternative oxygen delivery system according to an example embodiment.

FIG. 9 is a perspective view of an alternative oxygen delivery system 900 according to an example embodiment. System 900 includes a bridge portion 905 similar to system 100, as well as conduits 910 and perforations 915 supported between the mouth and nose of the wearer. Conduits 910 may be elongated to support more perforations to create the bolus of gas about the nostrils and the nose of the mouth of the wearer.

Figure 10:
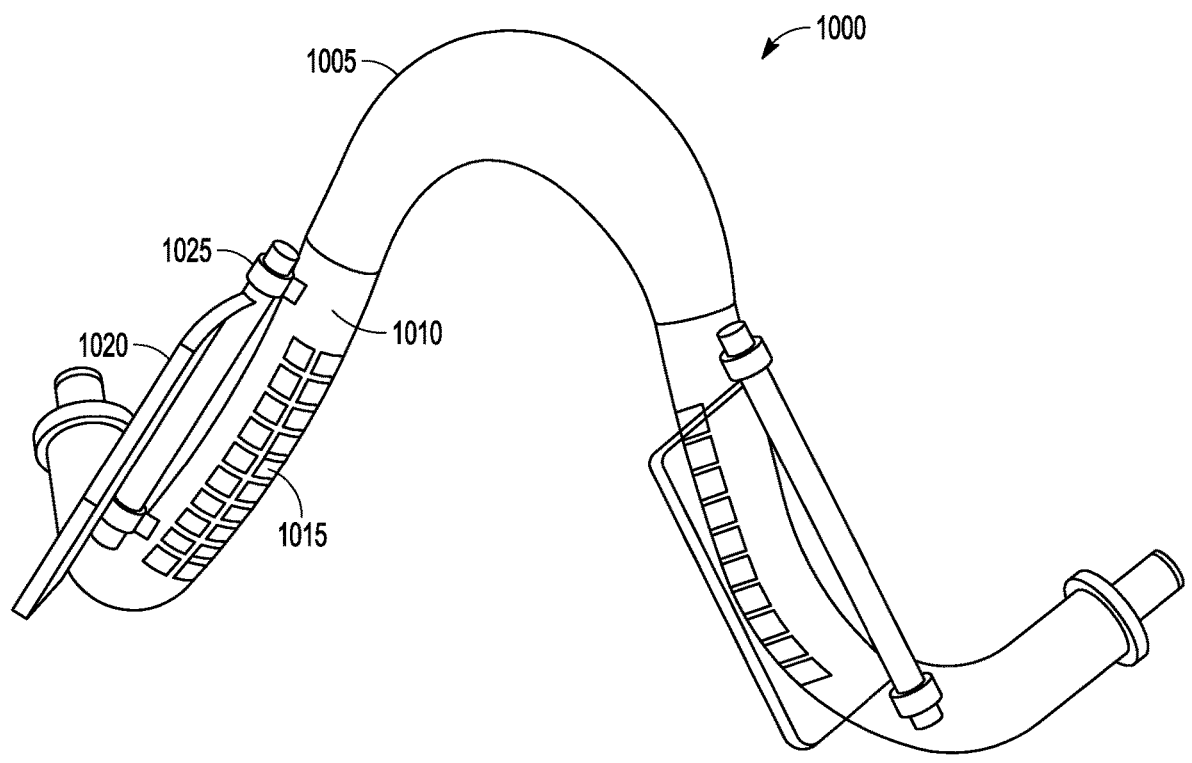
FIG. 10 is a perspective view of an alternative oxygen delivery system according to an example embodiment.

FIG. 10 is a perspective view of an alternative oxygen delivery system 1000 according to an example embodiment. System 1000 includes a bridge portion 1005 similar to system 100, as well as conduits 1010 and perforations 1015 supported between the mouth and nose of the wearer. Conduits 1010 may include panels 1020 rotatably coupled to the conduits via hinges 1025 to adjustably deflect gas from the perforations to create and shape the bolus of gas about the nostrils and the nose of the mouth of the wearer.

EXAMPLES

1. A gas delivery system, for providing gas to a wearer, includes a first body having a first cavity, the first body being supportable to a side of a nose and mouth of the wearer. A first adapter is coupled to receive gas from a gas supply and provide the gas to the first cavity. A plurality of first openings in the first body are positioned to create a bolus of gas about the nostrils of the nose and the mouth.

2. The gas delivery system of example 1 and further including a second body having a second cavity, the second body being supportable to a side of a nose and mouth of the wearer, a plurality of second openings in the second body, and a bridge support coupled between the first and second bodies to hold the first and second bodies on opposite sides of the mouth and nose of the wearer.

3. The gas delivery system of example 2 wherein the second cavity is configured to receive the gas.

4. The gas delivery system of example 3 wherein the second body includes a second adapter to receive gas from a gas supply and provide the gas to the second cavity.

5. The gas delivery system of any of examples 3-4 wherein the bridge support includes a conduit to provide gas from the first cavity to the second cavity.

6. The gas delivery system of any of examples 3-5 wherein the bridge support is moldable to a wearer's nose.

7. The gas delivery system of any of examples 1-6 wherein the openings are positioned between the nostrils and mouth of the wearer.

8. The gas delivery system of any of examples 1-7 wherein the openings include alternating louvers and exits from the first cavity.

9. The gas delivery system of example 8 wherein the louvers have rounded edges to reduce gas turbulence.

10. The gas delivery system of any of examples 1-9 and further including a baffle dividing a portion of the cavity into two chambers to divert a portion of the gas to first openings that are lower on the body than higher openings.

11. The gas delivery system of example 10 wherein the baffle extends between the first adapter and past at least one of the first openings that are higher than the lower openings.

12. The gas delivery system of any of examples 10 wherein the baffle is a concave plate that curves in conjunction with the first body to create the bolus of gas.

13. The gas delivery system of any of examples 1-12 wherein the first adapter includes a ledge to match an inner diameter of a gas supply tube to reduce gas turbulence between the gas supply tube and the first cavity.

14. The gas delivery system of any of examples 1-13 wherein the gas is oxygen.

15. An oxygen delivery system, for providing oxygen to a wearer, includes a first body having a first cavity, the first body being supportable to a side of a nose and mouth of the wearer, a first adapter to receive gas from a gas supply and provide the gas to the first cavity, a plurality of first openings in the body to create a bolus of gas about the nostrils of the nose and the mouth, a second body having a second cavity, the second body being supportable to a side of a nose and mouth of the wearer, a second adapter to receive gas from the gas supply and provide the gas to the second cavity, a plurality of second openings in the second body, and a bridge support coupled between the first and second bodies to hold the first and second bodies on opposite sides of the mouth and nose of the wearer.

16. The system of example 15 wherein the first and second cavities have rounded edges based on computational fluid dynamics to reduce oxygen turbulence.

17. A method includes receiving oxygen for distribution to a wearer of an oxygen distribution system, supporting the oxygen distribution system on a nose of a wearer, and flowing the oxygen to a plurality of openings of the oxygen distribution system, the openings being positioned to both sides of the wearer between a mouth and nostrils of the wearer so as not to obstruct direct access to the mouth and nostrils and to create a bolus of oxygen about the mouth and nostrils of the wearer.

18. The method of example 17 and further including diverting a portion of oxygen flow using a baffle to openings closer to the mouth of the wearer.

19. The method of example 18 and further including using louvers to direct the oxygen flow from the openings to create the bolus of oxygen.

20. The method of any of examples 18-19 and further including collecting air proximate the mouth and nose via a collection tube, providing the collected air exhausted to a gas analyzer, and determining a wearer respiration rate as a function of the collected air.

21. A gas delivery system, for providing gas to a wearer, includes a first body having a first cavity, the first body being supportable about a nose and mouth of the wearer, a first adapter coupled to the first body to receive gas from a gas supply and provide the gas to the first cavity, and a plurality of first openings in the first body to create a bolus of gas about the nostrils of the nose and the mouth.

Although a few embodiments have been described in detail above, other modifications are possible. For example, the logic flows depicted in the figures do not require the particular order shown, or sequential order, to achieve desirable results. Other steps may be provided, or steps may be eliminated, from the described flows, and other components may be added to, or removed from, the described systems. Other embodiments may be within the scope of the following claims.

The invention claimed is:

1. A gas delivery system, for providing gas to a wearer, comprising:
    a first body having a first cavity, the first body being supportable to a first side of a nose and a mouth of the wearer;
    a first adapter to receive gas from a gas supply and provide the gas to the first cavity;
    a plurality of first openings in the first body configured to create a bolus of gas about nostrils of the nose and the mouth; and
    a baffle within the first cavity to divert a portion of the gas to lower openings of the plurality of first openings that are lower on the first body than higher openings of the plurality of openings.

2. The gas delivery system of claim 1, further comprising:
    a second body having a second cavity, the second body being supportable to a second side of the nose and the mouth of the wearer;
    a plurality of second openings in the second body; and
    a bridge support coupled between the first and second bodies configured to hold the first and second bodies on opposite sides of the nose and the mouth of the wearer.

3. The gas delivery system of claim 2 wherein the second cavity is configured to receive the gas.

4. The gas delivery system of claim 3 wherein the second body further comprises a second adapter to receive the gas from a gas supply and provide the gas to the second cavity.

5. The gas delivery system of claim 3 wherein the bridge support includes a conduit to provide the gas from the first cavity to the second cavity.

6. The gas delivery system of claim 3 wherein the bridge support is moldable to the nose of the wearer.

7. The gas delivery system of claim 1 wherein the plurality of first openings are configured to be positioned between the nostrils and the mouth of the wearer.

8. The gas delivery system of claim 1, wherein the baffle divides a portion of the first cavity into two chambers to divert the portion of the gas to the lower openings.

9. The gas delivery system of claim 8 wherein the baffle extends between the first adapter and the higher openings.

10. The gas delivery system of claim 8 wherein the baffle is a concave plate that curves in conjunction with the first body to create the bolus of gas.

11. The gas delivery system of claim 1 wherein the first adapter includes a ledge to match an inner diameter of a gas supply tube to reduce gas turbulence between the gas supply tube and the first cavity.

12. The gas delivery system of claim 1 wherein the gas is oxygen.

13. A gas delivery system, for providing gas to a wearer, comprising:
    a first body having a first cavity, the first body being supportable to a first side of a nose and a mouth of the wearer;

a first adapter to receive gas from a gas supply and provide the gas to the first cavity; and a plurality of first openings in the first body configured to create a bolus of gas about nostrils of the nose and the mouth, wherein the plurality of first openings comprise alternating louvers through which the gas exits from the first cavity.

14. The gas delivery system of claim 13 wherein the louvers have rounded edges to reduce gas turbulence.

15. An oxygen delivery system, for providing oxygen to a wearer, comprising:

a first body having a first cavity, the first body being supportable to a first side of a nose and a mouth of the wearer;

a first adapter to receive gas from a gas supply and provide the gas to the first cavity;

a plurality of first openings in the body configured to create a bolus of gas about nostrils of the nose and the mouth;

a first baffle within the first cavity to divert a portion of the gas to lower openings of the plurality of first openings that are lower on the first body than higher openings of the plurality of first openings;

a second body having a second cavity, the second body being supportable to a second side of the nose and the mouth of the wearer;

a plurality of second openings in the second body;

a second baffle within the second cavity to divert a portion of the gas to lower openings of the plurality of second openings that are lower on the second body than higher openings of the plurality of second openings;

a second adapter to receive gas from the gas supply and provide the gas to the second cavity; and a bridge support coupled between the first and second bodies configured to hold the first and second bodies on opposite sides of the mouth and the nose of the wearer.

16. The system of claim 15 wherein the first and second cavities have rounded edges based on computational fluid dynamics to reduce oxygen turbulence.

17. A method comprising:

receiving oxygen for distribution to a wearer of an oxygen distribution system;

supporting the oxygen distribution system on a nose of the wearer; and flowing the oxygen to a plurality of openings of the oxygen distribution system, the plurality of openings being positioned to both sides of the wearer between a mouth and nostrils of the wearer so as not to obstruct direct access to the mouth and the nostrils and to create a bolus of oxygen about the mouth and the nostrils of the wearer via a baffle configured to divert the oxygen to first openings of the plurality of openings that are lower on the oxygen distribution system than higher openings of the plurality of openings.

18. The method of claim 17, further comprising diverting a portion of oxygen flow using the baffle to openings of the plurality of openings that closer to the mouth of the wearer than other openings of the plurality of openings.

19. The method of claim 18, further comprising using louvers to direct the oxygen flow from the plurality of openings to create the bolus of oxygen.

20. The method of claim 18, further comprising:

collecting air proximate the mouth and the nose via a collection tube;

providing the collected air exhausted to a gas analyzer; and determining a respiration rate of the wearer as a function of the collected air.

21. A gas delivery system, for providing gas to a wearer, comprising:

a first body having a first cavity, the first body being supportable about a nose and a mouth of the wearer;

a first adapter coupled to the first body to receive gas from a gas supply and provide the gas to the first cavity;

a plurality of first openings in the first body configured to create a bolus of gas about nostrils of the nose and the mouth; and a baffle dividing a portion of the first cavity into two chambers to divert the portion of the gas to lower openings of the plurality of first openings.

\* \* \* \* \*